US009902984B2

(12) United States Patent
Dekany et al.

(10) Patent No.: US 9,902,984 B2
(45) Date of Patent: Feb. 27, 2018

(54) FERMENTATIVE PRODUCTION OF OLIGOSACCHARIDES

(71) Applicant: Glycom A/S, Hørsholm (DK)

(72) Inventors: Gyula Dekany, Sinnamon Park (AU);
Pauline Peltier-Pain, Orleans (FR);
Dóra Molnár-Gábor, Budapest (HU);
Markus Hederos, Svedala (SE)

(73) Assignee: GLYCOM A/S, Hørsholm (DK)

( * ) Notice: Subject to any disclaimer, the term of this patent is extended or adjusted under 35 U.S.C. 154(b) by 0 days.

(21) Appl. No.: 14/915,421

(22) PCT Filed: Sep. 5, 2014

(86) PCT No.: PCT/DK2014/050272
§ 371 (c)(1),
(2) Date: Feb. 29, 2016

(87) PCT Pub. No.: WO2015/032412
PCT Pub. Date: Mar. 12, 2015

(65) Prior Publication Data
US 2016/0208302 A1    Jul. 21, 2016

(30) Foreign Application Priority Data
Sep. 6, 2013    (DK) .................. 2013 70498

(51) Int. Cl.
*C12P 19/18*    (2006.01)
*C07H 3/02*     (2006.01)
*C07H 3/06*     (2006.01)
*C12P 19/04*    (2006.01)
*C12P 19/00*    (2006.01)
*C07H 1/00*     (2006.01)

(52) U.S. Cl.
CPC ................ *C12P 19/18* (2013.01); *C07H 1/00* (2013.01); *C07H 3/02* (2013.01); *C07H 3/06* (2013.01); *C12P 19/00* (2013.01); *C12P 19/04* (2013.01); *C12Y 302/01051* (2013.01)

(58) Field of Classification Search
CPC ...................................................... C12P 19/18
See application file for complete search history.

(56) References Cited

U.S. PATENT DOCUMENTS

| 2009/0082307 | A1 | 3/2009 | Samain et al. |
| 2012/0208181 | A1 | 8/2012 | Merighi et al. |

FOREIGN PATENT DOCUMENTS

| EP | 0102535      | 3/1984  |
| EP | 2728009      | 5/2014  |
| WO | WO9715683    | 5/1997  |
| WO | WO0104341    | 1/2001  |
| WO | WO2005040430 | 5/2005  |
| WO | WO2010070104 | 6/2010  |
| WO | WO2010070616 | 6/2010  |
| WO | WO2010115934 | 10/2010 |
| WO | WO2010115935 | 10/2010 |
| WO | WO2010142305 | 12/2010 |
| WO | WO2011144213 | 11/2011 |
| WO | WO2012034996 | 3/2012  |
| WO | WO2012097950 | 7/2012  |
| WO | WO2012112777 | 8/2012  |
| WO | WO2013046180 | 4/2013  |
| WO | WO2013046181 | 4/2013  |
| WO | WO2013087884 | 6/2013  |
| WO | WO2013182206 | 12/2013 |
| WO | WO2014048439 | 4/2014  |
| WO | WO2014090261 | 6/2014  |

OTHER PUBLICATIONS

Li, M et al., "Characterization of a Novel alpha-1,2-Fucosyltransferase of *Escherichia coli* O128:B12 and Functional Investigation of Its Common Motif," Biochemistry, 2008, vol. 47, pp. 378-387.
Extended European Search Report dated Aug. 10, 2017 for EP Patent Application No. 14842725.5, filed on Sep. 5, 2014.
Baumgartner, F. et al, "Construction of *Escherichia coli* strains with chromosomally integrated expression cassettes for the synthesis of 2'-fucosyllactose", Microbial Cell Factories, Internet article: http://www.microbialcellfactories.com/content/12/1/40, 12(40):1-13, (2013).
Drouillard, S. et al, "Large-scale synthesis of H-antigen oligosaccharides by expressing *Helicobacter pylori* (alpha) 1,2-fucosyltransferase in metabolically engineered *Escherichia coli* cells", Angew. Chem. Int. Ed. vol. 45, pp. 1778-1780, (2006).
Fernandez-Mayoralas, A. et al, "Synthesis of 3- and 2'-fucosyl-lactose and 3,2-difucosyl-lactose from partially benzylated lactose derivatives", Carbohydrate Research, vol. 154, pp. 93-101, (1986).
Freeze, H. et al, "Chapter 4: Glycosylation precursors", Essentials of Glycobiology, 2nd edition (Eds. A Varki et al.), Cold Spring Harbour Laboratory Press, (2009).
Gramer, M. et al, "Purification and characterization of (alpha)-L-fucosidase from Chinese hamster ovary cell culture supernatant", Glycobiology, 4(5):611-616, (1994).
Lee, W. et al, "Whole cell biosynthesis of a functional oligosaccharide, 2'-fucosyllactose, using engineered *Escherichia coli*", Microbial Cell Factories, Internet article: http://www.microbialcellfactories.com/content/11/1/48, 11(48):1-9, (2012).
Ishizuka, Y. et al, "Three-dimensional structure of fucosyllactoses in an aqueous solution", Journal of Carbohydrate Chemistry, 18:5:523-533, (1999).
Randrianstoa, M., "Synthése microbiologique des antigénes glucidiques des groupes sanguins", Thése de Doctorat soutenue le, a l' Université Joseph Fourier, Grenoble, France, pp. 64-66, (Sep. 30, 2008).

(Continued)

*Primary Examiner* — Karen Cochrane Carlson
(74) *Attorney, Agent, or Firm* — Neal, Gerber & Eisenberg LLP

(57) ABSTRACT

The present application discloses a method of making a mixture of 2'-FL and DFL in high yield by culturing, with lactose, a genetically modified cell having a recombinant gene that encodes a single fucosyl transferase. The resulting mixture of 2'-FL and DFL can be subjected to hydrolysis initiated by an acid or mediated by a fucosidase to produce fucose in high yields.

15 Claims, 2 Drawing Sheets

(56) References Cited

OTHER PUBLICATIONS

Saari, P. et al, A novel chromatographic production scale separation process for L-fucose, Journal of Liquid Chromatography & Related Technologies, vol. 32, pp. 2050-2064, (2009).
Samain, E. et al, "Production of 0-acetylated and sulfated chitooligosaccharides by recombinant *Escherichia coli* strains harboring different combinations of nod genes", Journal of Biotechnology, vol. 72, pp. 33-47, (1999).
Takeo, K. et al, "Synthesis of lactodifucotetraose", Carbohydrate Research, vol. 141, pp. 159-164, (1985).
Vanhooren, P. et al, "L-Fucose: occurrence, physiological role, chemical, enzymatic and microbial synthesis", J. Chem. Technol. Biotechnol. vol. 74, pp. 479-497, (1999).

FERMENTATIVE PRODUCTION OF OLIGOSACCHARIDES

CROSS REFERENCE TO RELATED APPLICATIONS

This is a national stage filing in accordance with 35 U.S.C. § 371 of PCT/DK2014/050272, filed Sep. 5, 2014, which claims the benefit of the priority of Denmark Patent Application PA 2013 70498, filed Sep. 6, 2013, the contents of each are incorporated herein by reference.

FIELD OF THE INVENTION

The present invention relates to a method of making a mixture of 2'-FL (2'-O-fucosyllactose, Fuc($\alpha$1-2)Gal($\beta$1-4)Glc) and DFL (difucosyl-lactose, Fuc($\alpha$1-2)Gal($\beta$1-4)[Fuc($\alpha$1-3)]Glc) by fermentation and the use of the mixture for making fucose (6-deoxy-galactose).

BACKGROUND OF THE INVENTION

Fucose is one of the so-called rare monosaccharides. It is found in a wide variety of natural products from many different sources in both D- and L-forms. Mammalian cells can make fucosylated glycans, such as ABO blood group antigens and several human milk oligosaccharides. There is fucose in eggs of sea urchins and in frog spawn. Fucose is present in polysaccharides from plants such as seaweed (in the form of fucoidan, sulphated fucose polymer); gum tragacanth, potato, kiwi fruit, soybean, winged bean varieties, canola, etc. In plants, fucose is typically associated with plant polysaccharides, which are often highly branched structures having L-fucopyranosyl units either at the ends of or within the polysaccharide chains. Both N- and O-glycosyl chains of human or animal glycoproteins can contain fucose bound to the termini of the carbohydrate chains. Furthermore, extracellular polysaccharides from various bacteria, fungi and micro-algae also contain fucose. The fucosylation process in all natural living cells has two common features: it is mediated by a fucosyl transferase enzyme, which carries the fucosyl residue to an appropriate acceptor; and it forms an activated fucose nucleotide, i.e., GDP-fucose, not fucose in free form.

Interest in fucose, particularly L-fucose, in free form has recently increased because of its potential usefulness in treating various diseases, inflammatory conditions and disorders relating to the human immune system. Fucose has also been used in the cosmetics, for skin moisturizing, skin regenerating, as an anti-aging agent and for preventing skin inflammation.

Fucose has been obtained from natural sources, synthesized chemically or enzymatically from monosaccharides and produced by microbe-assisted processes.

From natural sources, fucose containing oligosaccharides have been isolated from biomass, such as algae, by extraction, and then the oligosaccharides have been hydrolysed to provide complex mixtures of fucose and related sugars and derivatives. Recovery of the fucose has typically required sophisticated separation techniques such as chromatography with anion or cation exchange resins, dialysis, fractional crystallization, etc., depending on the nature of the accompanying sugars or sugar-related compounds (e.g. WO 2005/040430, P. Saari et. al. *J. Liquid Chrom. Rel. Technol.* 32, 2050 (2009)).

Chemical syntheses of fucose have involved chemical modifications of common monosaccharides like L-galactose, D-galactose, L-arabinose, D-glucose, D-mannose and L-rhamnose (see review: P. T. Vanhooren et al. *J. Chem. Technol. Biotechnol.* 74, 479 (1999), WO 2011/144213, WO 2013/046180, WO 2013/046181). Enzymatic syntheses of fucose and its analogs have been carried out from fuculose-6-phosphate using a multienzymatic system (see WO 97/15683).

Bacteria from *Alcaligenes* sp. have also been cultured to produce fucose-rich extracellular polysaccharides, from which the fucose has been released by acidic hydrolysis (see EP-A-102535). Similarly, a bacterial strain from the family Enterobacteriaceae has been found able to produce L-fucose containing polysaccharides under aerobic fermentation conditions, from which the fucose has been separated and isolated by acidic hydrolysis and many purification steps (see WO 2012/034996).

Fucosylated lactoses, particularly 2'-FL and DFL, have recently been synthesized by lengthy sequences of chemical process steps (see WO 2010/070616, WO 2010/115934, WO 2010/115935, Takeo et al. *Carbohydr. Res,* 141, 159 (1985), Fernandez-Mayoralas et al. *Carbohydr. Res,* 154, 93 (1986)). Lower cost ways of producing fucosylated lactoses have, however, been sought, such as by fermentation with transformed *E. coli* (see Drouillard et al. *Angew. Chem, Int, Ed,* 45, 1778 (2006); M. Randriantsoa: *Synthèse microbiologique des antigènes glucidiques des groupes sanguins,* Thèse de Doctorat soutenue le 30 Sep. 2008 a l'Université Joseph Fourier, Grenoble, France; WO 2010/070104; WO 2010/142305; WO 2012/097950WO2012/112777; Lee et al. *Microb. Cell Fact,* 11:48 (2012); Baumgärtner et al. *Microb. Cell Fact.* 12:40 (2013)).

However, better methods have continued to be sought for the low-cost manufacture of fucosylated lactoses which could be hydrolysed to produce fucose at low cost.

SUMMARY OF THE INVENTION

A first aspect of this invention relates to a method of obtaining a mixture of 2'-FL and DFL in high yield, optionally containing FLU (2'-O-fucosyl-lactulose) and/or FFL ((Fuc($\alpha$1-2)Fuc($\alpha$1-2)Gal($\beta$1-4)Glc), comprising the step of culturing or fermenting, in an aqueous culture or fermentation medium containing lactose, a genetically modified cell, advantageously an *E. coli*, more advantageously a LacZ$^-$Y$^+$ *E. coli* cell, having a recombinant gene which encodes a single fucosyl transferase, advantageously a 1,2-fucosyl transferase, that is capable of modifying lactose or an intermediate in the biosynthetic pathway of 2'-FL from lactose and that is necessary for the synthesis of 2'-FL from lactose; the method being characterized by:

providing the lactose in the culture medium for more than 4 days, advantageously up to 7 days; and/or providing, in the culture medium, at least 50, advantageously at least 75, more advantageously at least 100, even more advantageously at least 125 grams of lactose per 1 liter of initial culture volume, advantageously in a continuous manner, so that the final volume of the culture medium is not more than three-fold, advantageously not more than two-fold, more advantageously less than two-fold of the volume of the culture medium before the culturing.

Advantageously, the resulting mixture of 2'-FL and DFL in the culture medium is at least 75, more advantageously at least 100, particularly at least 115 grams per liter of the culture medium. More advantageously, the weight of the DFL in the resulting mixture comprises advantageously at least 2.5%, more advantageously at least 5%, even more advantageously at least 10%, particularly at least 20% of the weight of the 2'-FL.

Also advantageously, a carbon-based substrate, more advantageously glucose, is provided in the culture medium to produce exponential cell growth of the genetically modified cell before the culturing step. Also advantageously, a carbon and energy source, more advantageously glycerol, is added to the culture medium with the lactose. Also advantageously, the genetically modified cell secretes the mixture of 2'-FL and DFL into an extracellular space of the culture medium during the culturing step.

A second aspect of this invention relates to a method of obtaining fucose, particularly L-fucose, in high yield, comprising the step of subjecting to hydrolysis initiated by an acid or mediated by a fucosidase:

2'-FL and/or DFL, preferably at least DFL, separated from a mixture comprising 2'-FL and DFL which has been obtained by the method of the first aspect of the invention and in which the weight of the DFL comprises advantageously at least 2.5%, more advantageously at least 5%, even more advantageously at least 10%, particularly at least 20% of the weight of the 2'-FL.

Advantageously, the hydrolysis is carried out with a strong acid, more advantageously with sulfuric acid.

A third aspect of this invention relates to a method of obtaining 2'-FL from lactose in high yield comprising the step of: culturing, in an aqueous culture medium containing lactose, a genetically modified cell, preferably an *E. coli*, advantageously an *E. coli* LacZ⁻Y⁺ cell, having a recombinant gene that encodes a fucosyl transferase, advantageously a 1,2-fucosyl transferase, capable of modifying lactose or an intermediate in the biosynthetic pathway of 2'-FL from lactose and that is necessary for the synthesis of 2'-FL from lactose; the method being characterized by providing the lactose in the culture medium for more than 4 days, advantageously up to 7 days; and/or providing, in the culture medium, at least 50, advantageously at least 75, more advantageously at least 100, even more advantageously at least 125 grams of the lactose per 1 liter of initial culture volume, advantageously in a continuous manner, so that the final volume of the culture medium is not more than three-fold, advantageously not more than two-fold, more advantageously less than two-fold, of the volume of the culture medium before the culturing.

Advantageously, the resulting 2'-FL in the culture medium is at least 65, more advantageously at least 80, particularly at least 90, grams per liter of the culture medium. Also advantageously, the genetically modified cell secretes 2'-FL into the extracellular space of the culture medium during the culturing step. Also advantageously, a carbon-based substrate, advantageously glucose, is provided in the culture medium to produce exponential cell growth of the genetically modified cell before the culturing step. Also advantageously, a carbon and energy source, more advantageously glycerol, is added to the culture medium with the lactose.

A fourth aspect of the invention relates to a mixture which can be obtained by the method of the first aspect of the invention and which comprises 2'-FL and
DFL+FLU or
DFL FFL or
DFL+FLU+FFL.

A fifth aspect of the invention relates to providing FFL.

BRIEF DESCRIPTION OF THE FIGURES

The invention will be described in further detail hereinafter with reference to the accompanying figures, in which.

DETAILED DESCRIPTION OF THE INVENTION

Figure 1:
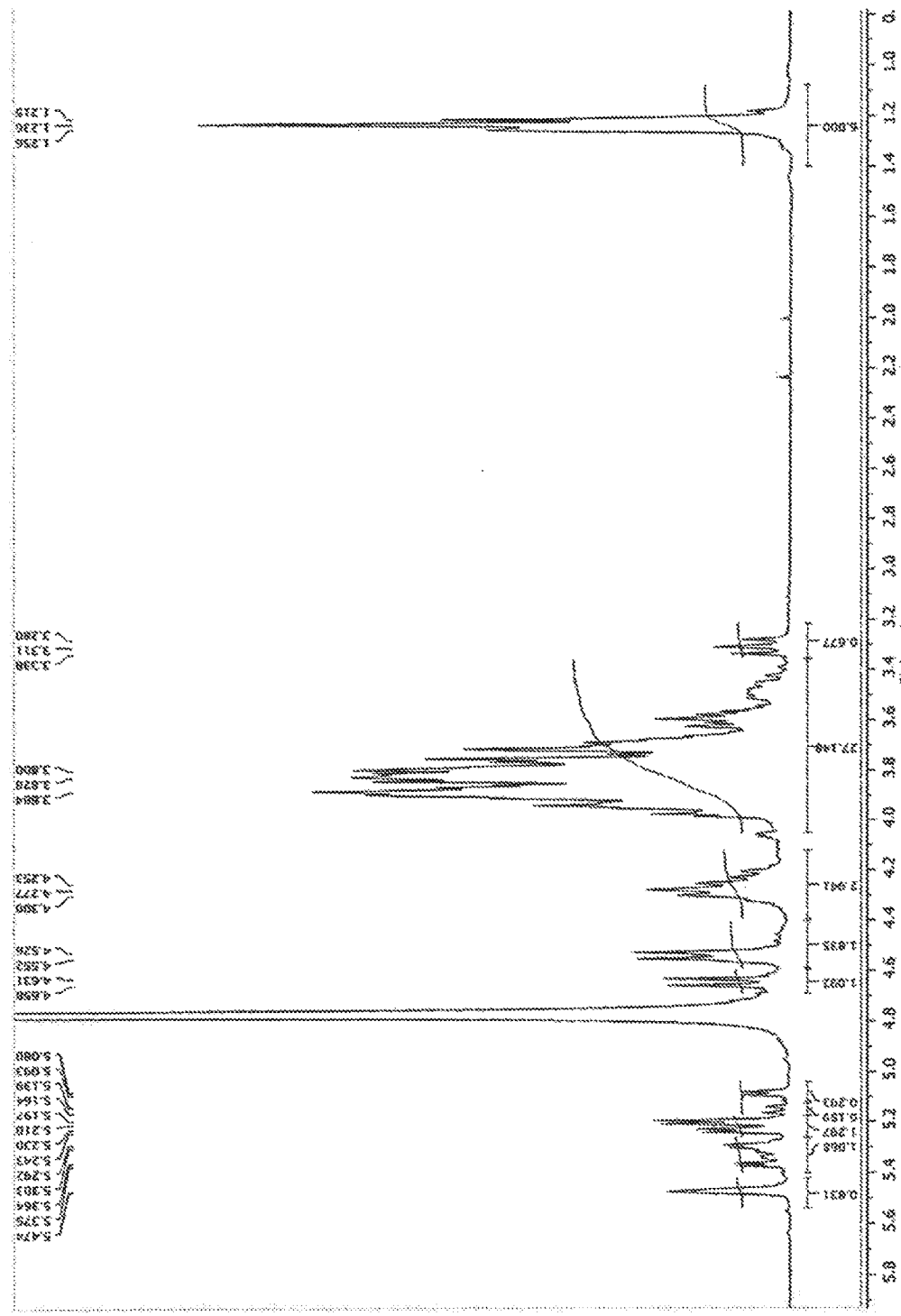
FIG. 1 shows the $^1$H NMR spectrum of FFL (300 MHz, D$_2$O, TSS reference).

In accordance with this invention, it has been surprisingly discovered that a genetically modified cell having a single glycosyl transferase which is a fucosyl transferase, preferably a 1,2-fucosyl transferase, in an aqueous fermentation broth or culture medium containing lactose, can:

produce a mixture containing very significant amounts of both 2'-FL and DFL and then secrete the mixture into the extracellular space of the culture medium, from which the mixture can then be easily separated.

This 2'-FL DFL mixture can subsequently be hydrolysed by treating the mixture with an acid or a fucosidase in a simple manner to provide high yields of fucose at relatively low cost.

In this invention, the term "genetically modified cell" preferably means a cell in which at least one DNA sequence has been added to, deleted from or changed in its genome, so that the has a changed phenotype. This change in phenotype alters the characteristics of the genetically modified cell from that of the wild type cell. Thus, the genetically modified cell can perform at least an additional chemical transformation, when cultured or fermented, due to the added or changed DNA that encodes the expression of at least one enzyme not found in the wild type cell, or the genetically modified cell cannot perform a chemical transformation due to the deleted, added or changed DNA that encodes the expression of an enzyme found in the wild type cell. The genetically modified cell can be produced by well-known, conventional genetic engineering techniques. The genetically modified cell can be bacteria or a yeast but preferably is a bacterium. Preferred bacteria include *Escherichia coli*, *Bacillus* spp. (e.g. *Bacillus subtilis*), *Campylobacter pylori*, *Helicobacter pylori*, *Agrobacterium tumefaciens*, *Staphylococcus aureus*, *Thermophilus aquaticus*, *Azorhizobium caulinodans*, *Rhizobium leguminosarum*, *Neisseria gonorrhoeae*, *Neisseria meningitis*, *Lactobacillus* spp., *Lactococcus* spp., *Enterococcus* spp., *Bifidobacterium* spp., *Sporolactobacillus* spp., *Micromomospora* spp., *Micrococcus* spp., *Rhodococcus* spp., *Pseudomonas*, particularly *E. coli*.

In carrying out the method of the first aspect of this invention for making 2'-FL and DFL in high yield, a genetically modified cell having a single recombinant glycosyl transferase which is a 1,2-fucosyl transferase, preferably an α1,2-fucosyl transferase, capable of modifying an exogenous lactose acceptor or a necessary intermediate in the biosynthetic pathway of 2'-FL and DFL from lactose, is cultured in a culture medium containing lactose. The genetically modified cell used in the method of this invention is able to transfer a fucosyl residue of an activated sugar nucleotide to the internalized lactose, and, in case of DFL production, also able to transfer a second fucosyl residue to the previously formed fucosyl lactose, preferably 2'-FL. The gene or an equivalent DNA sequence thereof responsible for the above function, if it is recombinant, is introduced into the cell by known techniques, using an expression vector. The origin of the heterologous nucleic acid sequence can be any animal (including human) or plant, e.g. human FUT1 or FUT2 genes, wcfW gene from *Bacteroides fragilis*, futC gene from *Helicobacter pylori* or wbsJ gene from *E. coli*, all encoding α1,2-fucosyl transferase.

When carrying out this method, a fucosyl transferase mediated fucosylation reaction preferably takes place in which an activated sugar nucleotide, GDP-Fuc, serves as donor. The genetically modified cell is able to produce GDP-Fuc by a de novo pathway. In this regard, GDP-Fuc is made by the cell under the action of enzymes involved in the de novo biosynthetic pathway of GDP-Fuc in a stepwise reaction sequence starting from a simple carbon source like glycerol, fructose or glucose (for a review for monosaccharide metabolism see e.g. H. H. Freeze and A. D. Elbein: Chapter 4: *Glycosylation precursors*, in: Essentials of Glycobiology, 2nd edition (Eds. A. Varki et al.), Cold Spring Harbour Laboratory Press (2009). The enzymes involved in the de novo biosynthetic pathway of GDP-Fuc can be naturally present in the cell or introduced into the cell by means of gene technology or recombinant DNA techniques, all of them are parts of the general knowledge of the skilled person.

It should be emphasized, that the de novo synthesis of GDP-Fuc by the genetically modified cell is advantageous compared to in vitro versions of transfer fucosylation, as it avoids using the very expensive GDP-Fuc added exogenously, rather, this donor is formed by the cell in situ, and the phosphatidyl nucleoside leaving group is recycled in the cell.

Preferably in carrying out the method of the first aspect of this invention, the genetically modified cell is cultured in the presence of a carbon-based substrate such as glycerol, glucose, glycogen, fructose, maltose, starch, cellulose, pectin, chitin, sucrose etc., to internalize the lactose acceptor added in the cell where the fucosylation takes place. Preferably, the cell is cultured with glycerol and/or glucose and/or fructose, preferably glycerol.

The method of the first aspect of this invention also involves initially transporting the exogenous lactose, as an acceptor, from the culture medium into the genetically modified cell where it can be fucosylated to produce 2'-FL and/or DFL. Lactose can be added exogenously in a conventional manner to the culture medium, from which it can then be transported into the cell. The internalization of lactose should not, of course, affect the basic and vital functions or destroy the integrity of the cell. In one embodiment the internalization can take place via a passive transport mechanism during which lactose diffuses passively across the plasma membrane of the cell. The flow is directed by the concentration difference in the extra- and intracellular space with respect to lactose to be internalized, which lactose is supposed to pass from the place of higher concentration to the zone of lower concentration tending towards equilibrium. In other embodiment lactose can be internalized in the cell with the aid of an active transport mechanism, during which lactose diffuses across the plasma membrane of the cell under the influence of a transporter protein or permease of the cell. Lactose permease (LacY) has specificity towards lactose. Preferably, the internalization of the exogenous lactose takes place via an active transport mechanism.

The method of the first aspect is characterized in that the genetically modified cell used lacks enzymatic activity liable to degrade the lactose, 2'-FL, DFL, and the metabolic intermediates needed to make 2'-FL and DFL in the cell. In this regard, the β-galactosidase encoded by the LacZ gene, which hydrolyses lactose to galactose and glucose, is deleted (LacZ⁻ genotype). Alternatively, a genetically modified cell of LacZ⁻ genotype can further contain a functional β-galactosidase encoded by an exogenous LacZ gene expressing a low but detectable level of β-galactosidase activity in order to remove the optional residual lactose at the end of fermentation (see WO 2012/112777).

Preferably, an *E. coli* strain; particularly an *E. coli* LacZ⁻ Y⁺ strain, is used having only one recombinant glycosyl transferase which is an α1,2-fucosyl transferase, preferably an α1,2-fucosyl transferase encoded by the futC gene from *Helicobacter pylori*. For making a mixture of 2'-FL and DFL in high yield, the method preferably comprises: a) providing, to the culture medium, a carbon and energy source and at least 50, preferably at least 75, more preferably at least 100, even more preferably at least 125 grams of lactose based on 1 liter of initial culture volume. The method also preferably comprises: b) providing lactose to the culture medium for more than 4 days, preferably up to 7 days, preferably in a continuous manner. It is particularly preferred that the method comprises both steps a) and b). It is also particularly preferred that the final volume of the culture medium is not more than three-fold, more preferably not more than two-fold, particularly less than two-fold of the volume of the culture medium before providing the lactose and the carbon and energy source, preferably glycerol to the culture medium.

The 2'-FL+DFL mixture, optionally containing FLU (2'-O-fucosyl-lactulose) and optionally containing FFL (Fuc(α1-2)Fuc(α1-2)Gal(β1-4)Glc), that is produced in the culture medium preferably comprises at least 75 grams, more preferably at least 100 grams, particularly up to 115 grams per liter of the culture medium.

Preferably, the genetically modified *E. coli* LacZ⁻Y⁺ strain having only one recombinant glycosyl transferase which is an α1,2-fucosyl transferase, preferably encoded by the futC gene from *Helicobacter pylori*, to produce a mixture of 2'-FL and DFL in high yield as disclosed above, is cultured in the following way:
  (a) a first phase of exponential cell growth ensured by a carbon-based substrate, and
  (b) a second phase of cell growth limited by a carbon and energy source which is added continuously, together with the lactose that is added continuously.

Also preferably, the *E. coli* is cultured under conditions allowing the production of a culture with a high cell density. Also preferably, an inducer is also added to the culture medium, preferably isopropyl 3-D-thiogalactoside (IPTG).

The *E. coli* is preferably cultured continuously, preferably for at least 4 days, particularly up to 7 days, but not more than about 9-10 days, preferably at a temperature of 30 to 35° C., and preferably with continuous agitation, continuous aeration and continuous feeding of the carbon and energy source and lactose. In the mixture of 2'-FL and DFL so-produced in the culture medium, DFL preferably comprises at least 2.5 m/m %, more preferably at least 5 m/m %, even more preferably at least 10 m/m %, particularly at least 20 m/m % of the weight of 2'-FL.

According to another way to make a mixture of 2'-FL and DFL in high yield, an *E. coli* strain, preferably an *E. coli* LacZ⁻Y⁺ strain having only one recombinant glycosyl transferase which is an α1,2-fucosyl transferase, preferably an α1,2-fucosyl transferase encoded by the futC gene from *Helicobacter pylori*, is used in fermentation comprising:
providing the carbon and energy source, preferably glycerol, and lactose, preferably in a continuous manner, for more than 4 days, preferably up to 7 days.

The 2'-FL+DFL mixture, optionally containing FLU and optionally containing FFL, that is so-produced in the culture medium preferably comprises at least 75 grams, more preferably at least 100 grams, particularly up to 115 grams per liter of the culture medium.

Preferably, the genetically modified *E. coli* LacZ⁻Y⁺ strain having only one recombinant glycosyl transferase which is an α1,2-fucosyl transferase, preferably encoded by the futC gene from *Helicobacter pylori*, to produce a mixture of 2'-FL and DFL in high yield as disclosed above, is cultured in the following way:
(a) a first phase of exponential cell growth ensured by a carbon-based substrate, and
(b) a second phase of cell growth limited by a carbon and energy source which is added continuously, together with the lactose that is added continuously.

Also preferably, the *E. coli* is cultured under conditions allowing the production of a culture with a high cell density. Also preferably, an inducer is also added to the culture medium, preferably isopropyl β-D-thiogalactoside (IPTG).

The *E. coli* is cultured for at least 4 days, particularly up to 7 days, but not more than about 9-10 days, at a temperature of 30 to 35° C., and preferably with continuous agitation, continuous aeration and continuous feeding of the carbon and energy source and lactose. In the mixture of 2'-FL and DFL so-produced in the culture medium, DFL preferably comprises at least 2.5 m/m %, more preferably at least 5 m/m %, even more preferably at least 10 m/m %, particularly at least 20 m/m % of the weight of 2'-FL.

In accordance with a more preferable way to make a mixture of 2'-FL and DFL in high yield, an *E. coli* strain, preferably an *E. coli* LacZ⁻Y⁺ strain having only one recombinant glycosyl transferase which is an α1,2-fucosyl transferase, preferably an α1,2-fucosyl transferase encoded by the futC gene from *Helicobacter pylori*, is used in fermentation comprising:
providing the carbon and energy source, preferably glycerol, and at least 50, preferably at least 75, more preferably at least 100 grams of lactose based on 1 liter of initial culture volume, preferably in a continuous manner, preferably for more than 4 days, more preferably up to 7 days, preferably so that the final volume of the culture medium is not more than three-fold, more preferably not more than two-fold, even more preferably less than two-fold, of the volume of the culture medium before the culturing.

The 2'-FL+DFL mixture, optionally containing FLU and optionally containing FFL, that is produced in the culture medium preferably comprises at least 75 grams, more preferably at least 100 grams, particularly up to 115 grams per liter of the culture medium.

Preferably, the genetically modified *E. coli* LacZ⁻Y⁺ strain having only one recombinant glycosyl transferase which is an α1,2-fucosyl transferase, preferably encoded by the futC gene from *Helicobacter pylori*, to produce a mixture of 2'-FL and DFL in high yield as disclosed above, is cultured in the following way:
(a) a first phase of exponential cell growth ensured by a carbon-based substrate, and
(b) a second phase of cell growth limited by a carbon and energy source which is added continuously, together with the lactose that is added continuously.

Also preferably, the *E. coli* is cultured under conditions allowing the production of a culture with a high cell density. Also preferably, an inducer is also added to the culture medium, preferably isopropyl 3-D-thiogalactoside (IPTG).

The *E. coli* is cultured for at least 4 days, particularly up to 7 days, but not more than about 9-10 days, preferably at a temperature of 30 to 35° C., and preferably with continuous agitation, continuous aeration and continuous feeding of the carbon and energy source and lactose. In the mixture of 2'-FL and DFL so-produced in the culture medium, DFL preferably comprises at least 2.5 m/m %, more preferably at least 5 m/m %, even more preferably at least 10 m/m %, particularly at least 20 m/m % of the weight of 2'-FL.

At the end of culturing the *E. coli*, whatever way is followed, the 2'-FL+DFL mixture, optionally containing FLU and optionally containing FFL, can be accumulated both in the intra- and the extracellular matrix. The mixture can be transported to the supernatant in a passive way, i.e., it can diffuse outside across the cell membrane. The transport can be facilitated by one or more sugar efflux transporters, i.e. proteins that promote the effluence of sugar derivatives from the cell to the supernatant. The sugar efflux transporter(s) can be present exogenously or endogenously and can be overexpressed under the conditions of the fermentation to enhance the export of the oligosaccharide derivative produced. The specificity towards the sugar moiety of the product to be secreted can be altered by mutation by means of known recombinant DNA techniques. Preferably, the 2'-FL+DFL mixture accumulates in the extracellular matrix.

The 2'-FL+DFL mixture, made by fermentation, can then be separated in a conventional manner from the aqueous culture medium, in which the mixture was made.

A first step of separating the 2'-FL+DFL mixture from the culture medium preferably involves clarifying the culture medium to remove suspended particulates and contaminants, particularly cells, cell components, insoluble metabolites and debris produced by culturing the genetically modified cell. In this step, the aqueous culture medium, which contains 2'-FL and DFL, can be clarified in a conventional manner. Preferably, the culture medium is clarified by centrifugation and/or filtration.

A second step of separating the 2'-FL+DFL mixture from the culture medium preferably involves removing substantially all the proteins, as well as peptides, amino acids, RNA and DNA and any endotoxins and glycolipids that could interfere with the subsequent separation step, from the aqueous culture medium, preferably after it has been clarified. In this step, proteins and related impurities can be removed from the culture medium in a conventional manner. Preferably, proteins and related impurities are removed from the culture medium by ultrafiltration, tangential flow high-performance filtration, tangential flow ultrafiltration, affinity chromatography, ion exchange chromatography, hydrophobic interaction chromatography and/or gel filtration (i.e., size exclusion chromatography), particularly by chromatography, more particularly by ion exchange chromatography or hydrophobic interaction chromatography. With the exception of size exclusion chromatography, proteins and related impurities are retained by a chromatography medium or a selected membrane, while the 2'-FL+DFL mixture remains in the aqueous culture medium.

If desired, the 2'-FL and DFL in the aqueous culture medium can then be separated from each other and from the culture medium, after proteins and related impurities have been removed from the culture medium. This can be suitably done by subjecting the culture medium to chromatographic separation. This separation can be carried out in a chromatographic separation column, filled with a conventional acidic cationic ion exchange resin. The acidic cationic ion exchange resin can be in monovalent or divalent cationic form and is preferably in $H^+$, $K^+$, $Na^+$, $Mg^{2+}$ or $Ca^{2+}$ form, particularly $Ca^{2+}$. The chromatographic separation can be carried out in a conventional manner at a pH of the solution of 2 to 9 to separate the 2'-FL from the DFL. The eluent used in the chromatographic separation is preferably water, especially demineralized water, but aqueous salt solutions can also be used. Alcohols, such as ethanol, and aqueous alcohol mixtures can also be used. The separated 2'-FL can be used as a supplement in infant formulas and for treating various maladies in newborn infants.

The second aspect of the invention involves subjecting a mixture comprising 2'-FL and DFL and optionally containing FLU and optionally containing FFL, preferably as made by the method of the first aspect of the invention, to hydrolysis to produce fucose. From this mixture, before hydrolysis, proteins and related impurities have preferably been removed, and DFL preferably comprises at least 2.5 m/m %, more preferably at least 5 m/m %, even more preferably at least 10 m/m %, particularly at least 20 m/m % of the weight of 2'-FL. In making fucose, the mixture of 2'-FL and DFL is subjected to fucose hydrolysis mediated by a fucosidase or preferably initiated by an acid.

The 2'-FL+DFL mixture or the separated 2'-FL and/or DFL and/or any FLU and/or any FFL can be hydrolysed with a strong acid in an aqueous solution from room temperature up to reflux, preferably at a temperature about 40-60° C., more preferably at about 50° C., and preferably at a pH of no more than about 3. Preferred strong acids include the strong mineral acids, such as sulphuric acid, nitric acid, chloric acid, perchloric acid, hydrobromic acid, hydroiodic acid and hydrochloric acid and the strong organic acids, such as p-toluenesulfonic acid or benzenesulfonic acid, particularly sulfuric acid. A mixture of water and an organic protic or aprotic solvent which is stable under acidic conditions and fully or partially miscible with water, such as $C_1$-$C_6$ alcohols, acetone, THF, dioxane, ethyl acetate and MeCN, can be used as the solvent. The fucosyl groups can be hydrolysed from a lactose residue selectively before the interglycosidic linkage between galactose and glucose splits.

The acid in the resulting reaction mixture, containing free fucose, can subsequently be neutralized in a conventional manner by the addition of an equivalent amount of a base, and the resulting salt can be removed by biogel filtration. Alternatively, a heterogeneous anionic ion exchange resin, that was added for neutralization, can be removed by simple filtration. From the resulting neutralized and desalted reaction mixture, the fucose can be separated in a conventional manner from lactose and other by-products and then isolated in solid form by crystallization, lyophilisation, precipitation or spray-drying, or in syrupy form.

Alternatively, the 2'-FL+DFL mixture or the separated 2'-FL and/or DFL and/or any FLU and/or any FFL can be hydrolysed enzymatically. For this purpose, a fucosidase that can release fucosyl residues, preferably all the fucosyl residues, from 2'-FL and/or DFL and/or any FLU and/or any FFL is preferably used. The fucosidase can be any conventional fucosidase, such as those belonging to one of the following glycoside hydrolase families: GH29 or GH95. A preferred fucosidase is an α-L-fucosidase (EC 3.2.1.51), particularly, one of the α-L-fucosidases encoded by one of the genes publicly available under the following GenBank Database (GI) numbers:

| GI number in GenBank Database | Organisms |
| --- | --- |
| gi|4980806 | *Thermotoga maritima* MSB8 |
| gi|13816464 | *Sulfolobus solfataricus* P2 |
| gi|34451973 | *Bifidobacterium bifidum* JCM 1254 |
| gi|242345155 | *Bifidobacterium bifidum* JCM 1254 |
| gi|213524647 | *Bifidobacterium longum* subsp. *infantis* ATCC 15697 |
| gi|213522629 | *Bifidobacterium longum* subsp. *infantis* ATCC 15697 |
| gi|213522799 | *Bifidobacterium longum* subsp. *infantis* ATCC 15697 |
| gi|213524646 | *Bifidobacterium longum* subsp. *infantis* ATCC 15697 |
| gi|296182927 | *Bifidobacterium longum* subsp *longum* JDM 301 |
| gi|296182928 | *Bifidobacterium longum* subsp *longum* JDM 301 |
| gi|283103603 | *Bifidobacterium dentium* Bd1 |
| gi|190713109 | *Lactobacillus casei* BL23 |
| gi|190713871 | *Lactobacillus casei* BL23 |
| gi|190713978 | *Lactobacillus casei* BL23 |

If desired, more than one fucosidase can be used to enzymatically hydrolyse the 2'-FL+DFL mixture or the separated 2'-FL and/or DFL and/or any FLU and/or any FFL. In this regard, with a 1,2-α-L-fucosidase, the cleavage of the 3-O-fucosyl residue is not expected, and with a 1,3/4-α-L-fucosidase, the cleavage of the 2-O-fucosyl residue is not expected. Therefore, for fucose hydrolysis from 2-FL, preferably only a 1,2-α-L-fucosidase is used, and from a 2'-FL+DFL mixture optionally containing FLU and optionally containing FFL or from the separated DFL both types of fucosidases are preferably used. In a dual fucosidase hydrolysis method, the fucosidases can be added simultaneously or sequentially. In a sequential addition, if a 1,3/4-α-L-fucosidase is added first, the 2'-FL+DFL mixture optionally containing FLU and optionally containing FFL would be converted to a mixture of 2'-FL and fucose optionally containing FLU and optionally containing FFL, which mixture would then be treated with a 1,2-α-L-fucosidase to obtain a mixture of fucose and lactose optionally containing lactulose. Likewise, the separated DFL would be converted to a mixture of 2'-FL and fucose, which mixture would then be treated with a 1,2-α-L-fucosidase to obtain a mixture of fucose and lactose. In case of adding a 1,2-α-L-fucosidase first to a 2'-FL+DFL mixture optionally containing FLU and optionally containing FFL, a mixture of 3-FL and lactose optionally containing lactulose would be produced, to which would then be added a 1,3/4-α-L-fucosidase to get a mixture of fucose and lactose optionally containing lactulose. Likewise, from the separated DFL, a mixture of 3-FL and lactose would be produced after treatment with a 1,2-α-L-fucosidase, to which a 1,3/4-α-L-fucosidase would then be added to get a mixture of fucose and lactose.

After enzymatic hydrolysis, the fucosidase in the resulting reaction mixture, containing fucose and lactose and optionally lactulose can be denatured and centrifuged. The resulting solution can then be evaporated under reduced pressure. After lyophilisation, the dry residue can be dissolved in water, and the fucose can be purified by biogel chromatography with water or by reverse phase chromatography. From the purified fractions, the fucose can be isolated in solid form by crystallization, lyophilisation, precipitation or spray-drying, or in syrupy form.

If desired, the 2'-FL and DFL and/or any FLU and/or any FFL in the mixture produced by the method of the first aspect of the invention can be separated from each other after proteins and related impurities have been removed from the culture medium. This can be suitably done by subjecting the culture medium to chromatographic separation in a conventional manner. This separation can be carried out in a chromatographic separation column, filled with a conventional acidic cationic ion exchange resin. The acidic cationic ion exchange resin can be in monovalent or divalent cationic form and is preferably in $H^+$, $K^+$, $Na^+$, $Mg^{2+}$ or $Ca^{2+}$ form, particularly $Ca^{2+}$. The chromatographic separation can be carried out in a conventional manner at a pH of the solution of 2 to 9 to separate the 2'-FL from the DFL. The eluent used in the chromatographic separation is preferably water, especially demineralized water, but aqueous salt solutions can also be used. Alcohols, such as ethanol, and aqueous alcohol mixtures, can also be used.

Depending on how the separation of the 2'-FL in the aqueous culture medium from any carbohydrate type contaminants is carried out, the separated 2'-FL can still contain:
DFL or
DFL+FLU or
DFL+FFL or
DFL+FLU+FFL.

The resulting 2'-FL and/or DFL and/or any FLU and/or any FFL can then each be separately hydrolysed, as described above, to produce fucose. Alternatively, one or all of them can be used in a conventional manner as food additives, particularly for infant nutrition.

In the third aspect of the invention, a method is provided for obtaining 2'-FL from lactose in high yield by culturing, in an aqueous culture medium, a genetically modified cell, preferably an *E. coli*, having a recombinant gene which encodes a fucosyl transferase, preferably a 1,2-fucosyl transferase, that is capable of modifying lactose or an intermediate in the biosynthetic pathway of 2'-FL from lactose and that is necessary for the synthesis of 2'-FL from lactose. This method is characterized by providing the carbon and energy source, preferably glycerol, and
  adding at least 50, preferably at least 75, more preferably at least 100 even more preferably at least 125 grams of lactose based on 1 liter of initial culture volume, preferably in a continuous manner, preferably so that the final volume of the culture medium is not more than three-fold, more preferably not more than two-fold, even more preferably less than two-fold, of the volume of the culture medium before the culturing, and/or
  adding lactose, preferably in a continuous manner, for more than 4 days, preferably up to 7 days.

The 2'-FL so-produced in the culture medium preferably comprises at least 65 grams, more preferably at least 80 grams, particularly at least 90 per liter of the culture medium.

In carrying out the method of this invention for making 2'-FL in high yield, a genetically modified cell having a recombinant 1,2-fucosyl transferase, preferably an α1,2-fucosyl transferase, capable of modifying an exogenous lactose acceptor or a necessary intermediate in the biosynthetic pathway of 2'-FL from lactose is cultured in a culture medium containing lactose. The genetically modified cell used in the method of this invention is able to transfer a fucosyl residue of an activated sugar nucleotide to the internalized lactose. The gene or an equivalent DNA sequence thereof responsible for the above function, if it is recombinant, is introduced into the cell by known techniques, using an expression vector. The origin of the heterologous nucleic acid sequence can be any animal (including human) or plant, e.g. human FUT1 or FUT2 genes, wcfW gene from *Bacteroides fragilis*, futC gene from *Helicobacter pylori* or wbsJ gene from *E. coli*, all encoding α1,2-fucosyl transferase.

When carrying out of the third aspect of the invention, a fucosyl transferase mediated fucosylation reaction preferably takes place in which an activated sugar nucleotide, GDP-Fuc, serves as donor. The genetically modified cell is able to produce GDP-Fuc by a de novo pathway. In this regard, GDP-Fuc is made by the cell under the action of enzymes involved in the de novo biosynthetic pathway of GDP-Fuc in a stepwise reaction sequence starting from a simple carbon source like glycerol, fructose or glucose (for a review for monosaccharide metabolism see e.g. H. H. Freeze and A. D. Elbein: Chapter 4: *Glycosylation precursors*, in: Essentials of Glycobiology, 2nd edition (Eds. A. Varki et al.), Cold Spring Harbour Laboratory Press (2009)). The enzymes involved in the de novo biosynthetic pathway of GDP-Fuc can be naturally present in the cell or introduced into the cell by means of gene technology or recombinant DNA techniques, all of them are parts of the general knowledge of the skilled person.

It should be emphasized, that the de novo synthesis of GDP-Fuc by the genetically modified cell is advantageous compared to in vitro versions of transfer fucosylation, as it avoids using the very expensive GDP-Fuc added exogenously, rather, this donor is formed by the cell in situ, and the phosphatidyl nucleoside leaving group is recycled in the cell.

Preferably in carrying out the third aspect of the invention, the genetically modified cell is cultured in the presence of a carbon-based substrate such as glycerol, glucose, glycogen, fructose, maltose, starch, cellulose, pectin, chitin, sucrose etc., to internalize the lactose acceptor added in the cell where the fucosylation takes place. Preferably, the cell is cultured on a carbon and energy source, such as glycerol and/or glucose and/or fructose, preferably glycerol.

The method of the third aspect of this invention also involves initially transporting the exogenous lactose, as an acceptor, from the culture medium into the genetically modified cell where it can be fucosylated to produce 2'-FL. Lactose can be added exogenously in a conventional manner to the culture medium, from which it can then be transported into the cell. The internalization of lactose should not, of course, affect the basic and vital functions or destroy the integrity of the cell. In one embodiment the internalization can take place via a passive transport mechanism during which lactose diffuses passively across the plasma membrane of the cell. The flow is directed by the concentration difference in the extra- and intracellular space with respect to lactose to be internalized, which lactose is supposed to pass from the place of higher concentration to the zone of lower concentration tending towards equilibrium. In other embodiment lactose can be internalized in the cell with the aid of an active transport mechanism, during which lactose diffuses across the plasma membrane of the cell under the influence of a transporter protein or permease of the cell. Lactose permease (LacY) has specificity towards lactose. Preferably, the internalization of the exogenous lactose takes place via an active transport mechanism.

The method of the third aspect of the invention is characterized in that the genetically modified cell used lacks enzymatic activity liable to degrade the lactose, 2'-FL, and the metabolic intermediates needed to make 2'-FL in the cell.

In this regard, the β-galactosidase encoded by the LacZ gene, which hydrolyses lactose to galactose and glucose, is deleted (LacZ$^-$ genotype). Alternatively, a genetically modified cell of LacZ$^-$ genotype can further contain a functional β-galactosidase encoded by an exogenous LacZ gene expressing a low but detectable level of β-galactosidase activity in order to remove the optional residual lactose at the end of fermentation (see WO 2012/112777).

Preferably, the genetically modified *E. coli*, preferably an *E. coli* LacZ$^-$Y$^+$ strain having a recombinant glycosyl transferase which is an α1,2-fucosyl transferase, preferably encoded by the futC gene from *Helicobacter pylori*, to produce 2'-FL in high yield as disclosed above, is cultured in the following way:
(a) a first phase of exponential cell growth ensured by a carbon-based substrate, and
(b) a second phase of cell growth limited by a carbon and energy source which is added continuously, together with the lactose that is added continuously.

Also preferably, the *E. coli* is cultured under conditions allowing the production of a culture with a high cell density. Also preferably, an inducer is also added to the culture medium, preferably isopropyl β-D-thiogalactoside (IPTG).

Preferably, an *E. coli* strain, particularly an *E. coli* LacZ$^-$Y$^+$ strain, is used having an α1,2-fucosyl transferase, preferably an α1,2-fucosyl transferase encoded by the futC gene from *Helicobacter pylori*. For making 2'-FL in high yield, the method preferably comprises: a) providing, to the culture medium, a carbon and energy source and at least 50, preferably at least 75, more preferably at least 100, even more preferably at least 125 grams of lactose based on 1 liter of initial culture volume. The method also preferably comprises: b) providing lactose to the culture medium for more than 4 days, preferably up to 7 days, preferably in a continuous manner. It is particularly preferred that the method comprises both steps a) and b). It is also particularly preferred that the final volume of the culture medium is not more than three-fold, more preferably not more than two-fold, particularly less than two-fold, of the volume of the culture medium before providing the lactose and the carbon and energy source, preferably glycerol, to the culture medium.

The 2'-FL produced in the culture medium preferably comprises at least 65 grams, more preferably at least 80 grams, particularly up to 90 grams per liter of the culture medium.

Preferably, the genetically modified *E. coli* LacZ$^-$Y$^+$ strain having a recombinant α1,2-fucosyl transferase, preferably encoded by the futC gene from *Helicobacter pylori*, to produce 2'-FL in high yield as disclosed above, is cultured in the following way:
(a) a first phase of exponential cell growth ensured by a carbon-based substrate, and
(b) a second phase of cell growth limited by a carbon and energy source which is added continuously, together with the lactose that is added continuously.

Also preferably, the *E. coli* is cultured under conditions allowing the production of a culture with a high cell density. Also preferably, an inducer is also added to the culture medium, preferably isopropyl β-D-thiogalactoside (IPTG).

The *E. coli* is preferably cultured continuously, preferably at a temperature of 30 to 35° C., and preferably with continuous agitation, continuous aeration and continuous feeding of the carbon and energy source and lactose.

According to another way to make 2'-FL in high yield, an *E. coli* strain, preferably an *E. coli* LacZ$^-$Y$^+$ strain having an α1,2-fucosyl transferase, preferably an α1,2-fucosyl transferase encoded by the futC gene from *Helicobacter pylori*, is used in fermentation comprising:
providing the carbon and energy source, preferably glycerol, and lactose, preferably in a continuous manner, for more than 4 days, preferably up to 7 days.

2'-FL so-produced in the culture medium preferably comprises at least 65 grams, more preferably at least 80 grams, particularly up to 90 grams per liter of the culture medium.

Preferably, the genetically modified *E. coli* LacZ$^-$Y$^+$ strain having an al 2-fucosyl transferase, preferably encoded by the futC gene from *Helicobacter pylori*, to produce 2'-FL in high yield as disclosed above, is cultured in the following way:
(a) a first phase of exponential cell growth ensured by a carbon-based substrate, and
(b) a second phase of cell growth limited by a carbon and energy source which is added continuously, together with the lactose that is added continuously.

Also preferably, the *E. coli* is cultured under conditions allowing the production of a culture with a high cell density. Also preferably, an inducer is also added to the culture medium, preferably isopropyl β-D-thiogalactoside (IPTG).

The *E. coli* is cultured for at least 4 days, particularly up to 7 days, but not more than about 9-10 days, at a temperature of 30 to 35° C., and preferably with continuous agitation, continuous aeration and continuous feeding of the carbon and energy source and lactose.

In accordance with a more preferable way to make 2'-FL in high yield, an *E. coli* strain, preferably an *E. coli* LacZ$^-$Y$^+$ strain having an α1,2-fucosyl transferase, preferably an α1,2-fucosyl transferase encoded by the futC gene from *Helicobacter pylori*, is used in fermentation comprising:
providing the carbon and energy source, preferably glycerol, and at least 50, preferably at least 75, more preferably at least 100 grams of lactose based on 1 liter of initial culture volume, preferably in a continuous manner, preferably for more than 4 days, more preferably up to 7 days, preferably so that the final volume of the culture medium is not more than three-fold, more preferably not more than two-fold, even more preferably less than two-fold, of the volume of the culture medium before the culturing.

2'-FL so-produced in the culture medium preferably comprises at least 65 grams, more preferably at least 80 grams, particularly up to 90 grams per liter of the culture medium.

Preferably, the genetically modified *E. coli* LacZ$^-$Y$^+$ strain having an at 2-fucosyl transferase, preferably encoded by the futC gene from *Helicobacter pylori*, to produce 2'-FL in high yield as disclosed above, is cultured in the following way:
(a) a first phase of exponential cell growth ensured by a carbon-based substrate, and
(b) a second phase of cell growth limited by a carbon and energy source which is added continuously, together with the lactose that is added continuously.

Also preferably, the *E. coli* is cultured under conditions allowing the production of a culture with a high cell density. Also preferably, an inducer is also added to the culture medium, preferably isopropyl β-D-thiogalactoside (IPTG).

The *E. coli* is cultured for at least 4 days, particularly up to 7 days, but not more than about 9-10 days, preferably at a temperature of 30 to 35° C., and preferably with continuous agitation, continuous aeration and continuous feeding of the carbon and energy source and lactose.

At the end of culturing the *E. coli*, whatever way is followed, 2'-FL can be accumulated as a product both in the intra- and the extracellular matrix. The product can be transported to the supernatant in a passive way, i.e., it can diffuse outside across the cell membrane. The transport can be facilitated by one or more sugar efflux transporters, i.e. protein(s) that promote(s) the effluence of sugar derivatives from the cell to the supernatant. The sugar efflux transporter (s) can be present exogenously or endogenously and can be overexpressed under the conditions of the fermentation to enhance the export of 2'-FL produced. The specificity towards the sugar moiety of the product to be secreted can be altered by mutation by means of known recombinant DNA techniques. Preferably, 2'-FL accumulates in the extracellular matrix.

The 2'-FL product can then be separated in a conventional manner from the aqueous culture medium, in which the mixture was made.

A first step of separating the 2'-FL product from the culture medium preferably involves clarifying the culture medium to remove suspended particulates and contaminants, particularly cells, cell components, insoluble metabolites and debris produced by culturing the genetically modified cell. In this step, the aqueous culture medium, which contains 2'-FL, can be clarified in a conventional manner. Preferably, the culture medium is clarified by centrifugation and/or filtration.

A second step of separating the 2'-FL product from the culture medium preferably involves removing substantially all the proteins, as well as peptides, amino acids, RNA and DNA and any endotoxins and glycolipids that could interfere with the subsequent separation step, from the aqueous culture medium, preferably after it has been clarified. In this step, proteins and related impurities can be removed from the culture medium in a conventional manner. Preferably, proteins and related impurities are removed from the culture medium by ultrafiltration, tangential flow high-performance filtration, tangential flow ultrafiltration, affinity chromatography, ion exchange chromatography, hydrophobic interaction chromatography and/or gel filtration (i.e., size exclusion chromatography), particularly by chromatography, more particularly by ion exchange chromatography or hydrophobic interaction chromatography. With the exception of size exclusion chromatography, proteins and related impurities are retained by a chromatography medium or a selected membrane, while 2'-FL remains in the aqueous culture medium.

If necessary, 2'-FL in the aqueous culture medium can then be separated from any carbohydrate type contaminants, after proteins and related impurities have been removed from the culture medium. This can be suitably done by subjecting the culture medium to chromatographic separation. This separation can be carried out in a chromatographic separation column, filled with a conventional acidic cationic ion exchange resin. The acidic cationic ion exchange resin can be in monovalent or divalent cationic form and is preferably in $H^+$, $K^+$, $Na^+$, $Mg^{2+}$ or $Ca^{2+}$ form, particularly $Ca^{2+}$. The chromatographic separation can be carried out in a conventional manner at a pH of the solution of 2 to 9 to separate the 2'-FL from carbohydrate type impurities. The eluent used in the chromatographic separation is preferably water, especially demineralized water, but aqueous salt solutions can also be used. Alcohols, such as ethanol, and aqueous alcohol mixtures can also be used. The separated 2'-FL can be used as a supplement in infant formulas and for treating various maladies in newborn infants.

EXAMPLE

Producing 2'-FL and DFL in High Yield

Bacterial Strains and Inoculum Preparation:

Engineered *E. coli* was constructed from *E. coli* K strain in accordance with WO 01/04341 and Drouillard et al. *Angew. Chem. Int. Ed. Eng.* 45, 1778 (2006), by deleting genes that are liable to degrade lactose, the oligosaccharide products and their metabolic intermediates, inter alia the lacZ, lacA and wcaJ genes, maintaining manB, manC, gmd and wcaG genes involved in the GDP-fucose biosynthesis, and inserting *H. pylori* futC gene for α-1,2-fucosyl transferase, as only glycosyl transferase.

General Fermentation Procedure:

Glucose, glycerol, isopropyl thio-β-D-galactopyranoside (IPTG) and lactose were each sterilized at 120° C.

The culture was carried out in a 3 l fermenter containing 1.5 l of mineral culture medium (Samain et al. *J. Biotechnol.* 72, 33 (1999)). The temperature was kept at 33° C. and the pH regulated at 6.8 with 28% $NH_4OH$. The inoculum (1% of the volume of the basal medium) consisted in a LB medium and the culture of the producing strain. The exponential growth phase started with the inoculation and stopped until exhaustion of the carbon source (glucose 17.5 g/l) initially added to the medium. The inducer (isopropyl thio-β-D-galactopyranoside, IPTG, 1-2 ml of a 50 mg/ml solution) was added at the end of the exponential phase. Then a fed-batch was realized, using 1 l of a feed solution containing 500 g of glycerol and 160-200 g of lactose dissolved in water, which was added to the culture during 4-7 days. At the end of the fermentation, the 2'-FL concentration varied between 68-114 g/l, and the 2'-FL:DFL ratio varied between 80:20 to 88:12 in the 2'FL+DFL mixture, produced. Fucosylated lactulose FLU (2'-O-fucosyl-lactulose) was no more than 1% in this mixture, and FFL (Fuc(α1-2)Fuc(α1-2)Gal(β1-4)Glc) was also no more than 1% in this mixture.

Purification:

At the end of the fermentation, the culture was centrifuged for 25-40 min at 4500-6000 rpm at 20-25° C. The supernatant was kept and acidify to pH 3 using a H+ form resin. This resulted in the precipitation of the proteins. The resin was recovered by decantation and precipitated proteins removed by centrifugation for 25-40 min at 4500-6000 rpm at 20-25° C. The supernatant was passed through a H+ form ion-exchange resin column and immediately neutralized by passing through a free base form anion exchange resin column. The compounds were eluted with water or aqueous ethanol. The fractions containing the product were collected, concentrated and freeze-dried/crystallized/precipitated.

Identification of Compounds:

2'-FL was identified by HPLC using reference compound and its $^1H$ and $^{13}C$ NMR spectra were in good agreement with those published in WO 2010/115935.

DFL was identified by LC-MS and NMR. Its $^1H$ and $^{13}C$ resonances were assigned based on detailed analysis of standard one-($^1H$, $^{13}C$) and two-dimensional homo- and heterocorrelation (gDQCOSY, 2D-TOCSY, 2DNOESY, $^1H$-$^{13}C$ gHSQCAD, $^1H$-$^{13}C$ gHMBCAD) measurements. The spectral data (see Table 1) were in agreement within experimental error with those reported in the literature (Ishizuka et al. *J. Carbohydr. Chem.* 18, 523 (1999)).

TABLE 1

$^1$H and $^{13}$C resonance assignments for DFL in D$_2$O, 25° C. at 400 MHz (α/β ratio is 9/11)

| Ring | proton | δ (ppm) | multiplicity | J (Hz) | Carbon | δ (ppm) |
|---|---|---|---|---|---|---|
| Glucose-α | H-1 | 5.18 | d | 3.8 | C-1 | 94.8 |
| (glu) | H-2 | 3.78 | m | | C-2 | 75.5 |
| | H-3 | 3.92 | m | | C-3 | 77.5 |
| | H-4 | 3.86 | m | | C-4 | 75.3 |
| | H-5 | 3.92 | m | | C-5 | 73.5 |
| | H-6x | 3.92 | m | | C-6 | 62.5 |
| | H-6y | 3.84 | m | | | |
| Glucose-β | H-1 | 4.62 | d | 8.1 | C-1 | 98.7 |
| (glu) | H-2 | 3.49 | dd | 9.5, 8.1 | C-2 | 78.3 |
| | H-3 | 3.71 | m | | C-3 | 79.8 |
| | H-4 | 3.88 | m | | C-4 | 75.4 |
| | H-5 | 3.46 | m | | C-5 | 78.3 |
| | H-6x | 3.99 | m | | C-6 | 62.6 |
| | H-6y | 3.80 | m | | | |
| Fucose-a, | H-1 | 5.40 | d | 4.0 | C-1 | 101.1 |
| connected | H-2 | 3.80 | m | | C-2 | 70.8 |
| to | H-3 | 3.98 | m | | C-3 | 72.0 |
| α glucose | H-4 | 3.81 | m | | C-4 | 74.7 |
| (fu-a) | H-5 | 4.86 | q | 6.3 | C-5 | 69.3 |
| | CH$_3$ | 1.24 | d | 6.3 | CH$_3$ | 18.1 |
| Fucose-a, | H-1 | 5.45 | d | 4.0 | C-1 | 101.0 |
| connected | H-2 | 3.80 | m | | C-2 | 70.8 |
| to | H-3 | 3.98 | m | | C-3 | 71.9 |
| β glucose | H-4 | 3.80 | m | | C-4 | 74.7 |
| (fu-a) | H-5 | 4.87 | q | 6.3 | C-5 | 69.3 |
| | CH$_3$ | 1.24 | d | 6.3 | CH$_3$ | 18.1 |
| Galactose | H-1 | 4.49 | d | 7.9 | C-1 | 102.9 |
| (ga) | H-2 | 3.63 | m | | C-2 | 79.1 |
| | H-3 | 3.85 | m | | C-3 | 76.3 |
| | H-4 | 3.87 | m | | C-4 | 71.5 |
| | H-5 | 3.59 | m | | C-5 | 72.6 |
| | H-6x | 3.75 | m | | C-6 | 64.2 |
| | H-6y | 3.71 | m | | | |
| Fucose-b | H-1 | 5.28 | d | 3.3 | C-1 | 102.1 |
| (fu-b) | H-2 | 3.81 | m | | C-2 | 70.8 |
| | H-3 | 3.78 (3.76) | m | | C-3 | 72.4 |
| | H-4 | 3.82 | m | | C-4 | 74.4 |
| | H-5 | 4.29 (4.27) | q | 6.3 | C-5 | 69.6 |
| | CH$_3$ | 1.26 | d | 6.3 | CH$_3$ | 18.2 |

FLU (2'-O-fucosyl-lactulose) was identified by LC-MS and NMR. Resonance assignments were performed by using standard one and two dimensional $^1$H-$^1$H and $^1$H-$^{13}$C correlation experiments (gCOSY, 2DTOCSY, $^1$H-$^{13}$C-gHSQCAD, $^1$H-$^{13}$C-gHMBCAD). The equilibrium isomeric ratio in DMSO at 25° C. was β-furanose/β-pyranose/α-furanose=55/40/5.

TABLE 2

$^1$H and $^{13}$C resonance assignments for 2'-O-fucosyl-lactulose in DMSO, 25° C. at 400 MHz (β-furanose isomer)

| Ring | proton | δ (ppm) | multiplicity | J (Hz) | carbon | δ (ppm) |
|---|---|---|---|---|---|---|
| β-D-fructo- | H-1x | 3.27 | dd | 11.6, 2.0 | C-1 | 62.6 |
| furanose | H-1y | 3.22 | dd | 11.6, 7.4 | | |
| | | | | | C-2 | 103.1 |
| | H-3 | 4.07 | m | | C-3 | 74.6 |
| | H-4 | 3.99 | m | | C-4 | 85.0 |
| | H-5 | 3.75 | m | | C-5 | 80.8 |
| | H-6x | 3.47 | m | | C-6 | 63.3 |
| | H-6y | 3.45 | m | | | |
| β-D | H-1 | 4.29 | d | 7.3 | C-1 | 101.2 |
| galactose | H-2 | 3.52 | m | | C-2 | 77.1 |
| | H-3 | 3.53 | m | | C-3 | 74.0 |
| | H-4 | 3.60 | m | | C-4 | 68.1 |
| | H-5 | 3.44 | m | | C-5 | 75.0 |
| | H-6x | 3.51 | m | | C-6 | 60.3 |
| | H-6y | | | | | |

TABLE 2-continued $^1$H and $^{13}$C resonance assignments for 2'-O-fucosyl-lactulose in DMSO, 25° C. at 400 MHz (β-furanose isomer)

| Ring | proton | δ (ppm) | multiplicity | J (Hz) | carbon | δ (ppm) |
|---|---|---|---|---|---|---|
| fucose | H-1 | 4.99 | d | 3.0 | C-1 | 100.1 |
| | H-2 | 3.57 | m | | C-2 | 69.6 |
| | H-3 | 3.54 | m | | C-3 | 72.9 |
| | H-4 | 3.46 | m | | C-4 | 71.6 |
| | H-5 | 4.06 | q | 6.4 | C-5 | 66.2 |
| | CH$_3$ | 1.04 | d | 6.4 | CH$_3$ | 16.4 |

Figure 2:
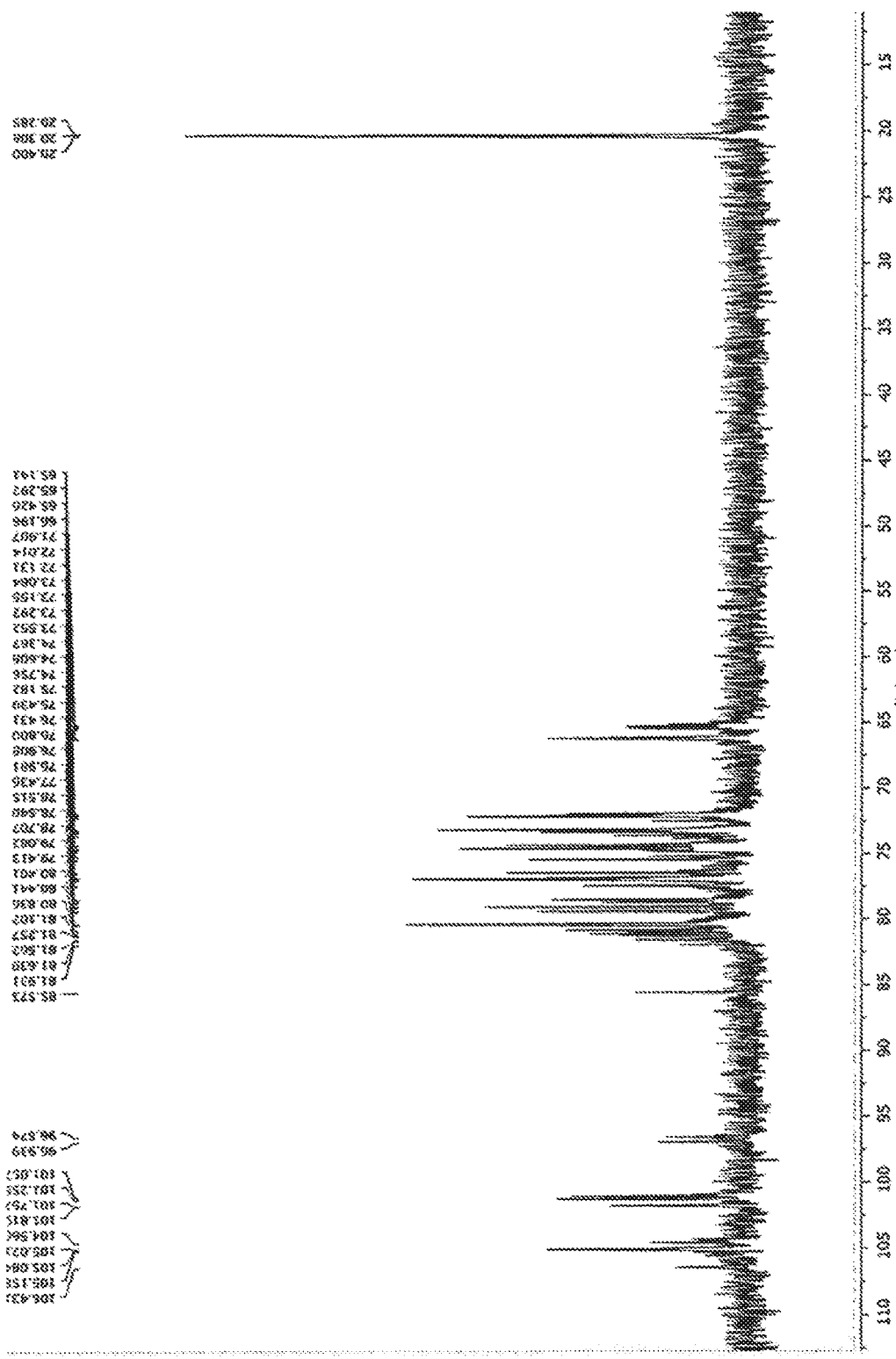
FIG. 2 shows the $^{13}$C NMR spectrum of FFL (75 MHz, D$_2$O, methyl group of fucose is set to 20.4 ppm).

Likewise, FFL (Fuc(α1-2)Fuc(α1-2)Gal(β1-4)Glc) was identified by LC-MS and NMR using standard one and two dimensional $^1$H-$^1$H and $^1$H-$^{13}$C correlation experiments (gCOSY, $^1$H-$^{13}$C-gHSQCAD). FIGS. 1 and 2 show its $^1$H and $^{13}$C NMR spectra, respectively.

The invention claimed is:

1. A method of obtaining a mixture of 2'-O-fucosyllactose and difucosyllactose,
said method comprising:
(a) transforming a genetically modified host cell having the ability to take up lactose with a gene encoding a fucosyltransferase that is under the control of an inducible promoter in a cell culture medium comprising a carbon source:
(b) allowing the culture to undergo an exponential growth phase until the carbon source is exhausted;
(c) inducing the expression of the fucosyltransferase;
(d) adding a carbon source and lactose in a common or separate feed solutions to the cell culture medium, wherein
(i) the carbon source and lactose feed solutions(s) is added in a continuous or stepwise manner for at least 4 days to the cell culture medium and wherein the addition of the carbon source and lactose feed solution(s) to the cell culture medium results in a final combined volume that does not exceed three-fold of the volume of the initial culture medium, and
(ii) the concentration of the lactose in the feed solution is sufficient to provide to the cell culture medium a daily amount of at least 15 g of lactose per initial liter of cell culture medium; and
(e) obtaining a mixture of 2'-O-fucosyllactose and difucosyllactose from the cell culture medium.

2. The method of claim 1, wherein the carbon source added in step (a) and the carbon source added in step (d) are independently selected from the group consisting of glycerol, sucrose, fructose and glucose.

3. The method of claim 1, wherein step (e) comprises obtaining a mixture 2'-O-fucosyllactose and difucosyllactose of at least 68 grams per liter of the cell culture medium.

4. The method of claim 3, wherein step (e) comprises obtaining a mixture 2'-O-fucosyllactose and difucosyllactose of at least 75 grams per liter of the cell culture medium.

5. The method of claim 3, wherein the mixture further comprises one or more by-products selected from the group consisting of 2'-O-fucosyllactulose and Fuc(α1-2)Fuc(α1-2)Gal(β1-4)Glc, or a combination thereof.

6. The method of claim 1, wherein the carbon source and lactose feed solution(s) is added in a continuous or stepwise manner for 4 to 7 days.

7. The method of claim 1, wherein the addition of lactose to the cell culture medium comprises adding a total of at least 75 grams of lactose per 1 liter of initial culture volume before step (e).

8. The method of claim 7, wherein the addition of lactose to the cell culture medium comprises adding a total of at least 100 grams of lactose per 1 liter of initial culture volume before step (e).

9. A method of obtaining 2'-O-fucosyllactose, said method comprising:
(a) transforming a genetically modified host cell having the ability to take up lactose with a gene encoding a fucosyltransferase that is under the control of an inducible promoter in a cell culture medium comprising a carbon source;
(b) allowing the culture to undergo an exponential growth phase until the carbon source is exhausted;
(c) inducing the expression of the fucosyltransferase;
(d) adding a carbon source and lactose in a common or separate feed solutions to the cell culture medium, wherein
(i) the carbon source and lactose feed solutions(s) is added in a continuous or stepwise manner for at least 4 days to the cell culture medium and wherein the addition of the carbon source and lactose feed solution(s) to the cell culture medium results in a final combined volume that does not exceed three-fold of the volume of the initial culture medium, and
(ii) the concentration of the lactose in the feed solution is sufficient to provide to the cell culture medium a daily amount of at least 15 g of lactose per initial liter of cell culture medium; and
(e) obtaining 2'-O-fucosyllactose from the cell culture medium.

10. The method of claim 9, wherein the carbon source added in step (a) and the carbon source added in step (d) are independently selected from the group consisting of glycerol, sucrose, fructose and glucose.

11. The method of claim 9, wherein step (e) comprises obtaining 2'-O-fucosyllactose of at least 65 grams per liter of the cell culture medium.

12. The method of claim 11, wherein the cell culture medium comprising 2'-O-fucosyllactose further comprises one or more by-products selected from the group consisting of difucosyllactose, Fuc($\alpha$1-2)Fuc($\alpha$1-2)Gal($\beta$1-4)Glc, and 2'-O-fucosyllactulose or a combination thereof.

13. The method of claim 9, wherein the carbon source and lactose is added in a continuous or stepwise manner for 4 to 7 days.

14. The method of claim 9, wherein the addition of lactose to the cell culture medium comprises adding a total of at least 75 grams of lactose per 1 liter of initial culture volume before step (e).

15. The method of claim 14, wherein the addition of lactose to the cell culture medium comprises adding a total of at least 100 grams of lactose per 1 liter of initial culture volume before step (e).

\* \* \* \* \*